United States Patent [19]

Cirjak et al.

[11] Patent Number: 4,504,371

[45] Date of Patent: Mar. 12, 1985

[54] PROCESS FOR THE PHOTOCATALYTIC ISOMERIZATION OF OLEFINS UTILIZING A MIXED METAL CLUSTER

[75] Inventors: Larry M. Cirjak, Burton; Lynne Sutherland, Cleveland, both of Ohio

[73] Assignee: The Standard Oil Company, Cleveland, Ohio

[21] Appl. No.: 579,258

[22] Filed: Feb. 13, 1984

[51] Int. Cl.³ .................. B01J 19/12; C07C 5/23; C07C 5/25

[52] U.S. Cl. .................. 204/158 R; 204/162 R; 585/670

[58] Field of Search .................. 204/158 R, 162 R; 585/670

[56] References Cited

U.S. PATENT DOCUMENTS

| | | | |
|---|---|---|---|
| 3,806,531 | 4/1974 | Koerner et al. | 204/158 R |
| 4,287,378 | 9/1981 | Pennella | 585/643 |
| 4,330,382 | 5/1982 | Yardley et al. | 204/157.1 R |
| 4,332,654 | 6/1982 | Yates | 204/158 R |
| 4,338,173 | 7/1982 | Yardley et al. | 204/162 R |
| 4,394,858 | 7/1983 | Giordano et al. | 204/158 R |

OTHER PUBLICATIONS

Journal of American Chem. Soc., vol. 101, No. 1, (Jan. 3, 1979), pp. 273–275, Graff et al.
Knight et al., "New Polynuclear Carbonyl Complexes Containing Iron with Cobalt or Rhodium", *Journal Chemical Society (A)*, 1970, pp. 654–658.
Hsieh et al., "New Nickel-Cobalt, Nickel-Iron and Nickel-Manganese Polynuclear Carbonyl Complexes", *Journal of Organometallic Chemistry*, 1971, pp. 125–132.

*Primary Examiner*—Howard S. Williams
*Attorney, Agent, or Firm*—Thomas P. Schur; Joseph G. Curatolo; Larry W. Evans

[57] ABSTRACT

A novel process for the isomerization of olefins which employs a photocatalytic mixed metal cluster, wherein a solution of the olefin and the cluster is irradiated causing the cluster to become catalytically active and to isomerize the olefin. The photocatalytic mixed metal cluster has the empirical formula:

$$(C_nR_{n'})_a Fe_b M_c (CO)_d L_e$$

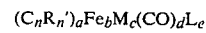

wherein n is five; wherein R' is selected from the group consisting of hydrogen, methyl, ethyl, acetyl, formyl, bromine, chlorine and fluorine; wherein M is a transition metal other than iron selected from the group consisting of Mo, Ru, Rh, Sc, Ti, V, Cr, Mn, Co, Ni, Cu and Zn; wherein L is a Group V type ligand; and further wherein a is from about one to five, b and c are from about one to five and b plus c is between two and six, d is from about five to 18 with the proviso that d is always equal to or greater than b plus c, and e is from about 0 to 18. A second novel process for the isomerization of olefins also employs a photocatalytic mixed metal cluster and irradiation wherein the cluster is first irradiated causing it to become catalytically active, and is then combined with an olefin to form a complex allowing the olefin to be isomerized.

26 Claims, No Drawings

PROCESS FOR THE PHOTOCATALYTIC ISOMERIZATION OF OLEFINS UTILIZING A MIXED METAL CLUSTER

TECHNICAL FIELD

The present invention is directed toward a process for the isomerization of olefins which is practiced by irradiating a solution of an olefin and of a photocatalyst and then collecting the isomerized olefin. The photocatalyst comprises (1) iron and another transition metal bonded thereto; and (2) suitable ligands to form a polynuclear complex.

The present invention is further directed toward a process for the isomerization of olefins which is practiced by first irradiating a photocatalyst which comprises (1) iron and another transition metal bonded thereto; and (2) suitable ligands to form a polynuclear complex, and then adding this now catalytically active complex to a solution containing an olefin; thus effecting the isomerization.

BACKGROUND ART

The isomerization of olefins is a well known process which is commonly performed utilizing elevated temperature and/or various mononuclear catalysts. Only recently has research in this area been directed toward photocatalysts and/or transition metal complexes. For example, U.S. Pat. No. 4,287,378 discloses the disproportionation, proportionation and/or isomerization of olefins utilizing electromagnetic radiation and mononuclear transition metal oxide catalysts such as magnesium oxide.

U.S. Pat. No. 4,332,654 is directed toward a process to form silylethers which utilizes an active catalyst formed from an irradiated transition metal carbonyl complex precursor. The complexes are polynuclear but are not mixed metal clusters.

U.S. Pat. No. 4,338,173 discloses a process for the catalytic isomerization of olefins which comprises exposing the combination of an olefin and a mononuclear transition metal complex, both in a gaseous state, to optical radiation.

Lastly, two journal articles, one by Knight, et al entitled "New Polynuclear Carbonyl Complexes Containing Iron with Cobalt or Rhodium" appearing in the *Journal of American Chemical Society* (1970), and the second by Hsieh, et al entitled "New Nickel-Cobalt, Nickel-Iron and Nickel-Manganese Polynuclear Carbonyl Complexes" appearing in the *Journal of Organometallic Chemistry* (1970), detail methods for the preparation of mixed metal clusters. Neither article discloses the utilization of light to initiate or increase catalytic activity of these mixed metal clusters.

Thus, while the art provides processes for the isomerization of olefins employing photocatalytic techniques, and also provides for the general synthesis of various metal clusters, the art has not disclosed any processes utilizing a photochemically activated polynuclear complex comprising iron and another transition metal and suitable ligands, wherein the iron atoms and the transition metal atoms are bonded directly together.

DISCLOSURE OF THE INVENTION

In general, one process of the present invention for the isomerization of olefins comprises the steps of: (1) forming a solution of the olefin and a photocatalytic mixed metal cluster in the form of a polynuclear complex having the formula:

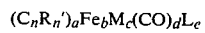
$(C_nR_{n'})_a Fe_b M_c (CO)_d L_e$ wherein n is five and wherein R' is selected from the group consisting of hydrogen, methyl, ethyl, acetyl, formyl, bromine, chlorine and fluorine; wherein M is a transition metal other than iron selected from the group consisting of Mo, Ru, Rh, Sc, Ti, V, Cr, Mn, Co, Ni, Cu and Zn; wherein L is a Group V type ligand and further wherein a is from about one to five, b and c are from about one to five and b plus c is between two and six, d is from about five to 18 with the proviso that d is always equal to or greater than b plus c, and e is from about 0 to 18; (2) irradiating the solution and allowing isomerization to occur.

A second process of the present invention for the isomerization of olefins comprises the steps of: (1) irradiating a photocatalytic mixed metal cluster in the form of a polynuclear complex having the formula:

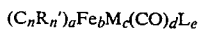
$(C_nR_{n'})_a Fe_b M_c (CO)_d L_e$ wherein n is five and wherein R' is selected from the group consisting of hydrogen, methyl, ethyl, acetyl, formyl, bromine, chlorine and fluorine; wherein M is a transition metal other than iron selected from the group consisting of Mo, Ru, Rh, Sc, Ti, V, Cr, Mn, Co, Ni, Cu and Zn; wherein L is a Group V type ligand and further wherein a is from about one to five, b and c are from about one to five and b plus c is between two and six, d is from about five to 18 with the proviso that d is always equal to or greater than b plus c, and e is from about 0 to 18; (2) combining this now catalytically active mixed metal cluster with an olefin to form a solution and allowing isomerization to occur.

PREFERRED MODE FOR CARRYING OUT THE INVENTION

An important feature of the present invention is that the disclosed processes for the isomerization of olefins combine two relatively new technologies in a novel manner. Practice of the present invention requires: (1) the presence of a photocatalytic mixed metal cluster comprising iron and another transition metal; and, (2) the utilization of irradiation.

The olefins suitable for the practice of the subject invention are generally defined as hydrocarbons which have at least one double bond. The olefins have the following formula:

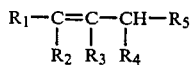
$$R_1-\underset{R_2}{C}=\underset{R_3}{C}-\underset{R_4}{CH}-R_5$$

wherein the total number of carbon atoms ranges from about four to 20 with the proviso that the number of carbon atoms of each R group, $R_1$ to $R_5$, ranges from about one to eight. There is a minimum number of carbon atoms because a true isomerization wherein the double bond moves from one position to another, changing the structure and physical properties of the compound, does not occur when the total number of carbon atoms is less than four. The double bond therein in effect does move, but the structure and physical properties of the compound remain the same.

The R groups, $R_1$ to $R_5$, of the aforementioned formula are selected from the group consisting of hydrogen, alkyl, hydroxyl, alkenyl and phenyl; and furthermore, cyclic compounds can be formed by the linkage of any two, three, four or all of the R groups.

Exemplary R groups specifically include methyl, ethyl, n-propyl, i-propyl, n-butyl, i-butyl, sec-butyl, t-butyl, vinyl, hydroxyl, phenyl, allenyl, cyclopropyl, cyclobutyl, cyclobutenyl, cyclopentenyl, ethynyl, 1-propynyl, 2-propynyl, 1-butynyl, 2-butynyl, 3-butynyl and the like. Specific suitable olefins include 1-pentene, cyclohexene, 1,3-cyclohexadiene and 1,5,9-cyclododecatriene.

The foregoing description and disclosure of suitable R groups and olefins are meant to be illustrative only of the many types of olefins which can be isomerized by the subject photocatalytic mixed metal clusters but should not be construed as exhaustive or limiting. Finally, further description and disclosure of suitable olefins is set forth in the aforementioned U.S. Pat. No. 4,338,173, column 2, therein, the subject matter of which is incorporated by reference.

The subject mixed metal cluster has the empirical formula:

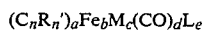

and importantly the iron atoms and the transition metal are bonded directly together. One potential advantage in these clusters and the metal-metal bonding is that they absorb more intensely throughout the spectrum than the traditional mononuclear transition metal complexes such as iron pentacarbonyl. Another advantage, specific to the metal-metal bond, is that the presence of different metals within the same complex can increase catalytic activity as compared to mononuclear complexes. Finally, these mixed metal clusters have been found, through IR, Mössbauer and NMR spectroscopy, to have carbonyl groups which bridge together in addition to the typical terminal ligand bonds, i.e., metal-ligand bonds, found in mononuclear complexes.

The specific $C_nR_n'$-type ligand of the subject mixed metal cluster has n equal to five and R' selected from the group consisting of hydrogen, methyl, ethyl, acetyl, formyl, bromine, chlorine, and fluorine with hydrogen being preferred, i.e., the ligand is cyclopentadienyl.

The specific transition metals other than iron which can be used are molybdenum, ruthenium, rhodium, scandium, titanium, vanadium, chromium, manganese, cobalt, nickel, copper and zinc with cobalt or nickel being preferred.

The preferred Group V type ligands represented by L in the aforementioned empirical formula have the general formula $XH_3$, $R''XH_2$, $R''X_2H$ and $R_3''X$ wherein X is selected from the group consisting of P, As and Sb and wherein R'' is selected from the group consisting of methyl, ethyl, phenyl, tert-butyl, ortho-tolyl and any oxy-compounds thereof wherein the R'' group is separated from the X component by an oxygen. The Group V type ligands can replace the carbonyl of the empirical formula as long as there is one carbonyl for each of the total number of iron and transition metal atoms present. The foregoing list of Group V type ligands is meant to be illustrative of only of the many types of Group V type ligands which can be substituted for the carbonyl ligand but should not be construed as exhaustive or limiting.

The necessary irradiation can be provided by a continuous or a pulsed light source with intensity between about 220 and 1400 nm. Exemplary sources includes sunlight, mercury lamps, argon ion laser, a KrF laser and a Nd/Yag laser. A mercury lamp with a monochromatic filter is preferred as it provides a convenient continuous source. It is operated at about 220 to 400 nm.

The actual isomerization of the olefin is measured in terms of overall quantum yield, $\Phi$. Quantum yield of product is defined as the ratio of product molecules to incident photons, i.e.:

$\Phi(prod)=$ Moles of Product/Moles of Photons.

The general reaction for the process wherein a solution of an olefin and a photocatalytic mixed metal cluster is first formed and then irradiated can be summarized as follows:

(1) Catalyst Precursor + Olefin $\xrightarrow{h\nu}$ Active Catalyst + Olefin (2) Active Catalyst + Olefin → Isomerized Olefin + Still Active Catalyst (3) Reuse of Active Catalyst from Step 2 to isomerize more of the olefin.

(4) Active Catalyst → Poisoned Catalyst Steps 1 and 2 are occurring nearly simultaneously, and steps 2 and 3 will repeat as long as the catalyst remains active and step 4 does not occur. In the preferred method, once the solution is irradiated for a specific time and quantity of photons, the light source is terminated. Thus step 1 is technically not repeated once the reaction begins though it is possible that the light source could be used indefinitely, but this is not preferred.

The general reaction for the process wherein the catalyst is first activated by irradiation and then added to an olefin to form a complex can be summarized as follows:

(A) Catalyst Precursor $\xrightarrow{h\nu}$ Active Catalyst (B) Active Catalyst + Olefin → Isomerized Catalyst + Still Active Catalyst (C) Reuse of active catalyst from step B to isomerize more of the olefin.

(D) Active Catalyst → Poisoned Catalyst Steps B and C will repeat as long as the catalyst remains active and step D does not occur.

Because in both embodiments there is a repetition of steps, the quantum yield can be greater than one, and a more accurate description of the quantum yield would be as follows:

$\Phi(prod) = \Phi(cat)$ (Turnover Number)

where
$\Phi(cat) = $ Moles of Catalyst/Moles of Photons so that
Turnover Number = Moles of Product/Moles of Catalyst.

Measurement of the quantum yield of product, $\Phi prod$, yields information about how well the photons of the irradiation are utilized. Ideally this value would be equivalent to the turnover number with the quantum yield of the catalyst, $\Phi cat$, equal to one, but the latter is typically less than one. The higher the turnover number is, the more efficient is the reaction; thus in a photocatalyst system, the turnover number is what is attempted to be optimized. The present mixed metal clusters do indeed optimize the turnover number inasmuch as a process employing one of these will produce a turnover number greater than one. Therefore, the subject mixed metal clusters offer an improvement over existing isomerization catalysts wherein processes utilizing the latter have turnover numbers of one or less.

The following examples demonstrate the practice of the embodiment of the present invention wherein first a solution is formed and then the solution is irradiated. It is to be understood that these examples are utilized merely for illustrative purposes and are not to be considered as limitations of the invention.

EXAMPLE 1

A photocatalytic mixed metal cluster, $(C_5H_5)CoFe_2(CO)_9$, was prepared by mixing a solution of $(C_5H_5)Co(CO)_2$ in hexane with a solution of $Fe_2(CO)_9$. The mixture was then cooled to yield the black crystals of $(C_5H_5)CoFe_2(CO)_9$. A $1\times10^{-2}M$ solution of these crystals was prepared utilizing the selected olefin, 1-pentene as the solvent. A 3 ml sample of the resulting solution was then irradiated with a continuous mercury lamp, having a monochromatic filter, at 366 nm for varying periods of time. Product analysis of the 1-pentene, i.e., how much 1-pentene, cis-2-pentene and trans-2-pentene present, was performed utilizing gas chromatography. By graphical techniques, the quantum yield of isomerization, Φprod, was found to range from about 13 to 22. The quantum yield of the catalyst, Φcat, was found in a separate test utilizing IR techniques, to be approximately one; thus, the turnover number also ranged from 13 to 22.

EXAMPLE 2

A photocatalytic mixed metal cluster, $(C_5H_5)_2Ni_2Fe_2(CO)_7$, was prepared by mixing a solution of $[(C_5H_5)Ni(CO)]_2$ in hexane with a solution of $Fe_2(CO)_9$. The mixture was then cooled to yield the dark green crystals of $(C_5H_5)_2Ni_2Fe_2(CO)_7$. A $1\times10^{-2}M$ solution of these crystals was prepared utilizing 1-pentene, and the irradiation and measurement procedures of Example 1 were repeated. The quantum yield of isomerization was found to range from about two to five.

Based upon the results appearing in Examples 1 and 2, it can be seen that processes utilizing a photocatalytic mixed metal cluster and irradiation to activate the photocatalyst provide an improvement in the process of isomerization of olefins inasmuch as the turnover number is greater than one. These results will be essentially the same for the alternative embodiment of the subject invention wherein the photocatalytic mixed metal cluster is first irradiated and catalytically activated, and then added to the olefin solution. The key is the general catalytic activation by irradiation of the photocatalytic mixed metal cluster. It is understood that the subject processes employing mixed metal clusters and irradiation can be practiced utilizing other clusters, light sources and olefins than the $(C_5H_5)CoFe_2(CO)_9$ or $(C_5H_5)_2Ni_2Fe_2(CO)_7$, the continuous source mercury lamp and 1-pentene exemplified herein; the examples having been provided merely to demonstrate practice of the subject invention. Other examples might include as the cluster $(C_5H_5)_2Mo_2Fe(CO)_8$, $(C_5H_5)RhFe_2(CO)_9$ and $(C_5H_5)_2RuFe_2(CO)_7$; as the light source a Nd/Yag laser; and, as the olefins cyclohexene, 1,3-cyclohexadiene and 1,5,9-cyclododecatriene. Those skilled in the art may readily select other mixed metal clusters, light sources and olefins according to the disclosure hereinabove.

Thus it is believed that any of the variables disclosed herein can readily be determined and controlled without departing from the spirit of the invention herein disclosed and described. Moreover, the scope of the invention shall include all modifications and variations that fall within the scope of the attached claims.

We claim:

1. A process for the isomerization of olefins comprising the steps of:
   forming a solution which comprises:
   an olefin; and,
   a photocatalytic mixed metal cluster, said cluster having the empirical formula $(C_nR_n')_aFe_bM_c(CO)_dL_e$ wherein n is five;
   wherein R' is selected from the group consisting of hydrogen, methyl, ethyl, acetyl, formyl, bromine, chlorine and fluorine;
   wherein M is a transition metal other than iron;
   wherein L is a Group V type ligand; and
   wherein
   a = 1 to 5
   b = 1 to 5
   c = 1 to 5
   b+c = 2 to 6
   d = 5 to 18 with the proviso
   that d is always equal to or greater than b+c, and
   e = 0 to 18;
   irradiating said solution and allowing isomerization to occur.

2. The process of claim 1, wherein the olefin has at least four carbon atoms and has the formula $$R_1-\underset{\underset{R_2}{|}}{C}=\underset{\underset{R_3}{|}}{C}-\underset{\underset{R_4}{|}}{C}H-R_5$$

wherein $R_1$ to $R_5$ are selected from the group consisting of hydrogen, alkyl, hydroxyl, alkenyl and phenyl.

3. The process of claim 2, wherein said olefin is selected from the group consisting of 1-pentene, cyclohexene, 1,3-cyclohexadiene and 1,5,9-cyclododecatriene.

4. The process of claim 1, wherein R' is hydrogen to yield a cyclopentadienyl ligand.

5. The process of claim 1, wherein said transition metal, M, is selected from the group consisting of Mo, Ru, Rh, Sc, Ti, V, Cr, Mn, Co, Ni, Cu and Zn.

6. The process of claim 5, wherein said transition metal, M, is Co.

7. The process of claim 5, wherein said transition metal, M, is Ni.

8. The process of claim 1, wherein said Group V type ligand, L, has the formula selected from the group consisting of $XH_3$, $R''XH_2$, $R_2''XH$ and $R_3''X$;
   wherein X is selected from the group consisting of P, As and Sb; and,
   wherein R'' is selected from the group consisting of methyl, ethyl, phenyl, tert-butyl, ortho-tolyl and oxy-compounds thereof wherein said X group and said R" group are separated by an oxygen.

9. The process of claim 1, wherein said photocatalytic mixed metal cluster is $(C_5H_5)CoFe_2(CO)_9$.

10. The process of claim 1 wherein said photocatalytic mixed metal cluster is $(C_5H_5)_2Ni_2Fe_2(CO)_7$.

11. The process of claim 1, wherein said irradiation has an intensity of from about 220 to 1400 nm.

12. The process of claim 11, wherein said irradiation is provided for by a laser.

13. The process of claim 11, wherein said irradiation is a mercury lamp with a monochromatic filter.

14. A process for the isomerization of olefins comprising the steps of:

irradiating a photocatalytic mixed metal cluster, said cluster having the empirical formula $(C_nR_n')_aFe_bM_c(CO)_dL_e$ wherein n is five;
wherein R' is selected from the group consisting of hydrogen, methyl, ethyl, acetyl, formyl, bromine, chlorine and fluorine;
wherein M is a transition metal other than iron;
wherein L is a Group V type ligand; and
wherein
a=1 to 5
b=1 to 5
c=1 to 5
b+c=2 to 6
d=5 to 18 with the proviso
that d is always equal to or greater than b+c; and
e=0 to 18;

combining said irradiated mixed metal cluster with an olefin to form a complex and allowing isomerization of the olefin to occur.

15. The process of claim 14, wherein the olefin has at least four carbon atoms and has the formula

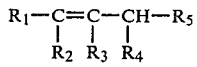

wherein $R_1$ to $R_5$ are selected from the group consisting of hydrogen, alkyl, hydroxyl, alkenyl and phenyl.

16. The process of claim 15, wherein said olefin is selected from the group consisting of 1-pentene, cyclohexene, 1,3-cyclohexadiene and 1,5,9-cyclododecatriene.

17. The process of claim 14, wherein R' is hydrogen to yield a cyclopentadienyl ligand.

18. The process of claim 14, wherein said transition metal, M, is selected from the group consisting of Mo, Ru, Rh, Sc, Ti, V, Cr, Mn, Co, Ni, Cu and Zn.

19. The process of claim 18, wherein said transition metal, M, is Co.

20. The process of claim 18, wherein said transition metal, M, is Ni.

21. The process of claim 14, wherein said Group V type ligand, L, has the formula selected from the group consisting of $XH_3$, $R''XH_2$, $R_2''XH$ and $R_3''X$;
wherein X is selected from the group consisting of P, As and Sb; and,
wherein R" is selected from the group consisting of methyl, ethyl, phenyl, tert-butyl, ortho-tolyl and oxy-compounds thereof wherein said X group and said R" group are separated by an oxygen.

22. The process of claim 14, wherein said photocatalytic mixed metal cluster is $(C_5H_5)CoFe_2(CO)_9$.

23. The process of claim 14, wherein said photocatalytic mixed metal cluster is $(C_5H_5)_2Ni_2Fe_2(CO)_7$.

24. The process of claim 14, wherein said irradiation has an intensity of from about 220 to 1400 nm.

25. The process of claim 24, wherein said irradiation is provided for by a laser.

26. The process of claim 24, wherein said irradiation is a mercury lamp with a monochromatic filter.

* * * * *